United States Patent
Nehrke et al.

(10) Patent No.: US 9,977,108 B2
(45) Date of Patent: May 22, 2018

(54) METAL RESISTANT MR IMAGING REFERENCE SCAN

(71) Applicant: KONINKLIJKE PHILIPS N.V., Eindhoven (NL)

(72) Inventors: Kay Nehrke, Hamburg (DE); Peter Boernert, Hamburg (DE); Johan Michiel Den Harder, Eindhoven (NL); Thomas Hendrik Rozijn, Eindhoven (NL)

(73) Assignee: KONIKLIJKE PHILIPS N.V., Eindhoven (NL)

( * ) Notice: Subject to any disclaimer, the term of this patent is extended or adjusted under 35 U.S.C. 154(b) by 516 days.

(21) Appl. No.: 14/432,931

(22) PCT Filed: Sep. 11, 2013

(86) PCT No.: PCT/IB2013/058447
§ 371 (c)(1),
(2) Date: Apr. 1, 2015

(87) PCT Pub. No.: WO2014/053927
PCT Pub. Date: Apr. 10, 2014

(65) Prior Publication Data
US 2015/0253406 A1    Sep. 10, 2015

Related U.S. Application Data

(60) Provisional application No. 61/708,680, filed on Oct. 2, 2012.

(51) Int. Cl.
*G01R 33/20* (2006.01)
*G01R 33/561* (2006.01)
(Continued)

(52) U.S. Cl.
CPC .......... *G01R 33/5611* (2013.01); *A61B 5/055* (2013.01); *G01R 33/246* (2013.01);
(Continued)

(58) Field of Classification Search
USPC ......................................... 324/309, 308, 317
See application file for complete search history.

(56) References Cited

U.S. PATENT DOCUMENTS 4,885,542 A    12/1989  Yao et al.
5,378,985 A *  1/1995  Hinks .............. G01R 33/56554
                                                        324/307
(Continued)

FOREIGN PATENT DOCUMENTS

EP    2461175 A1    6/2012

OTHER PUBLICATIONS

Hayter, C.L. et al "MRI after Arthroplasty: Comparison of MAVRIC and Conventional Fast Spin-Echo Techniques", Musculoskeletal Imaging, AJR, vol. 197, Sep. 20011, pp. W405-W410.
(Continued)

*Primary Examiner* — Vincent Q Nguyen

(57) ABSTRACT

The invention relates to a method of parallel MR imaging, wherein a reference scan is performed by means of a stimulated echo sequence including i) at least two preparation RF pulses ($\alpha$) radiated toward a portion of a body (10) during a preparation period (21), and ii) one or more reading RF pulses ($\beta$) radiated toward the portion of the body (10) during an acquisition period (22) temporally subsequent to the preparation period (21). One or more FID signals ($I_1$) and one or more stimulated echo signals ($I_2$) are acquired during the acquisition period (22). The spatial receive and/ or—if applicable—transmit4 sensitivity profiles of at least two RF coils (11, 12, 13) are derived from the acquired FID signals ($I_1$) and/or from the acquired stimulated echo signals
(Continued)

($I_2$). The parameters of the stimulated echo sequence are selected such that it is robust against susceptibility-induced artifacts. Moreover, 10 the invention relates to a MR device (1) and to a computer program for a MR device (1).

16 Claims, 2 Drawing Sheets

(51) Int. Cl.
    *G01R 33/24* (2006.01)
    *A61B 5/055* (2006.01)
    *G01R 33/34* (2006.01)
    *G01R 33/36* (2006.01)
    *G01R 33/385* (2006.01)

(52) U.S. Cl.
    CPC ............ *G01R 33/34* (2013.01); *G01R 33/36* (2013.01); *G01R 33/385* (2013.01)

(56) References Cited

U.S. PATENT DOCUMENTS

| | | | |
|---|---|---|---|
| 9,010,615 | B2 | 4/2015 | Yoshimoto et al. |
| 9,488,709 | B2 | 11/2016 | Den Harder et al. |
| 2007/0182410 | A1 | 8/2007 | Niemi |
| 2010/0240984 | A1 | 9/2010 | Fuderer |
| 2011/0001476 | A1 | 1/2011 | Morrell |
| 2011/0050223 | A1 | 3/2011 | Balcom et al. |
| 2011/0267055 | A1 | 11/2011 | Umeda |
| 2012/0001633 | A1* | 1/2012 | Fuderer .............. G01R 33/5611 324/309 |
| 2012/0133358 | A1 | 5/2012 | Broz |
| 2012/0301005 | A1 | 11/2012 | Fuderer |
| 2013/0088229 | A1 | 4/2013 | Van Den Brink |

OTHER PUBLICATIONS

Hargreaves, B.A. et al "Adaptive Slice Encoding for Metal Artifact Correction", Proceedings of the International Society for Magnetic Resonance in Medicine, vol. 18, 2010, pp. 3083.

Koch, K.M. et al "Multiple Resonant Frequency Offset Acquisitions for Imaging of Metallic Implants", Proceedings of the International Society for Magnetic Resonance in Medicine, vol. 16, 2008, pp. 1250.

Lu, W. et al "Towards Artifact-Free MRI near Metallic Implants", Proceedings of the International Society for Magnetic Resonance in Medicine, vol. 16, 2008, pp. 838.

Lu, Wenmian et al, SEMAC: Slice Encoding for Metal Artifact Correction in MRI ISMRM 2008, p. 838.

Helms, Gunther et al "Rapid Radiofrequency Field Mapping in Vivo using Single-Shot STEAM MRI", Magnetic Resonance in Medicine, Vo. 60, 2008, pp. 739-743.

Zhang, Q et al "Improving True-FISP Parallel Cine Imaging using a New Data-Acquisition Scheme for Coil Sensitivity Calibration", International Society for Magnetic Resonance in Medicine, Jan. 2003, pp. 2329.

Nehrke, Kay et al "Dream—a Novel Approach for Robust, Ultra-fast, Multislice B 1 Mapping", Magnetic Resonance in Medicine, vol. 68, No. 5, Jan. 2012, pp. 1517-1526.

Chen, W. et al "Parallel MRI near Metallic Implants", International Society for Magnetic Resonance in Medicine, vol. 17, Jan. 2009, p. 2783.

Monu, U.D. et al "B1 Mapping near Metallic Implants", Proc. International Society for Magnetic Resonance in Medicine, vol. 19, Jan. 2011, pp. 3175.

Guclu, C.C. et al "Correction of Dielectric Resonance Effect at 3T and above using B1-Mapping", Proc. International Society for Magnetic Resonance in Medicine, vol. 13, Jan. 2005, pp. 846.

Nehrke, K. et al "Fast B1 Mapping using a Steam-based Bloch-Siegert Preparation Pulse", Proc. International Society for Magnetic Resonance in Medicine, vol. 19, Jan. 2011, pp. 4411.

\* cited by examiner

METAL RESISTANT MR IMAGING REFERENCE SCAN

CROSS-REFERENCE TO PRIOR APPLICATIONS

This application is the U.S. National Phase application under 35 U.S.C. § 371 of International Application No. PCT/IB2013/058447, filed on Sep. 11, 2013, which claims the benefit of U.S. Provisional Patent Application No. 61/708,680, filed on Oct. 2, 2012. These applications are hereby incorporated by reference herein.

FIELD OF THE INVENTION

The invention relates to the field of magnetic resonance (MR) imaging. It concerns methods of MR imaging of at least a portion of a body. The invention also relates to a MR device and to a computer program to be run on a MR device.

BACKGROUND OF THE INVENTION

Image-forming MR methods which utilize the interaction between magnetic fields and nuclear spins in order to form two-dimensional or three-dimensional images are widely used nowadays, notably in the field of medical diagnostics, because for the imaging of soft tissue they are superior to other imaging methods in many respects, do not require ionizing radiation and are usually not invasive.

According to the MR method in general, the body of the patient to be examined is arranged in a strong, uniform magnetic field ($B_0$ field) whose direction at the same time defines an axis (normally the z-axis) of the co-ordinate system in which the measurement is based. The magnetic field splits different energy levels for the individual nuclear spins in dependence on the magnetic field strength and the specific spin properties. The spin system can be excited (spin resonance) by application of an electromagnetic alternating field (radio frequency (RF) field, also referred to as $B_1$ field) of defined frequency (so-called Larmor frequency, or MR frequency). From a macroscopic point of view the distribution of the individual nuclear spins produces an overall magnetization which can be deflected out of the state of equilibrium by application of an above mentioned electromagnetic pulse of appropriate radio frequency (RF pulse) while the corresponding $B_1$ magnetic field extends perpendicular to the z-axis, so that the magnetization performs a precessional motion about the z-axis. The precessional motion describes a surface of a cone whose angle of aperture is referred to as flip angle. The magnitude of the flip angle is dependent on the strength and the duration of the applied electromagnetic RF pulse. In the case of a so-called 90° pulse, the spins are deflected from the z axis to the transverse plane (flip angle) 90°.

After termination of the RF pulse, the magnetization relaxes back to the original state of equilibrium, in which the magnetization in the z direction is built up again with a first time constant $T_1$ (spin lattice or longitudinal relaxation time), and the magnetization in the direction perpendicular to the z direction relaxes with a second time constant $T_2$ (spin-spin or transverse relaxation time). The variation of the magnetization can be detected by means of one or more receiving RF coils which are arranged and oriented within an examination volume of the MR device in such a manner that the variation of the magnetization is measured in the direction perpendicular to the z-axis. The decay of the transverse magnetization is accompanied, after application of, for example, a 90° pulse, by a transition of the nuclear spins (induced by local magnetic field inhomogeneities) from an ordered state with the same phase to a state in which all phase angles are uniformly distributed (dephasing). The dephasing can be compensated by means of a refocusing pulse (for example a 180° pulse). This produces an echo signal (spin echo) in the receiving coils.

In order to realize spatial resolution in the body, linear magnetic field gradients extending along the three main axes are superposed on the uniform magnetic field, leading to a linear spatial dependency of the spin resonance frequency. The signal picked up in the receiving coils then contains components of different frequencies which can be associated with different locations in the body. The MR signal data obtained via the RF coils corresponds to the spatial frequency domain and is called k-space data. The k-space data are usually acquired along multiple lines with different phase encoding values to achieve sufficient coverage. Each line is digitized during read-out by collecting a number of samples. A set of k-space data is converted to a MR image by means of Fourier transformation.

With aging population and an increasing number of patients carrying metal implants, the need for MR imaging of soft tissue in the presence of metal increases. Metal resistant MR imaging is required to enable imaging this soft tissue for diagnosis of complications and follow-up after surgery. MR imaging near metal is typically compromised by susceptibility issues degrading the magnetic fields used for image formation locally. In diagnostic MR imaging scans, the susceptibility of the metal parts causes MR signal pile-up, signal voids and other geometric distortions. Multispectral imaging techniques like SEMAC (Lu et al, ISMRM 2008, p. 838) and MAVRIC (Koch et al, ISMRM 2008, p. 1250) have been proposed to counter susceptibility issues in diagnostic MR imaging scans at the cost of increased scan duration, which scales with the required frequency coverage.

Known parallel acquisition techniques can be used for accelerating the multispectral MR signal acquisition. A method in this category is SENSE (Sensitivity Encoding). SENSE and other parallel acquisition techniques use undersampled k-space data acquisition obtained from multiple RF receiving coils in parallel. In these methods, the (complex) signal data from the multiple RF receive coils are combined with complex weightings in such a way as to suppress undersampling artifacts (aliasing) in the finally reconstructed MR images. This type of complex RF coil array signal combination is sometimes referred to as spatial filtering and includes combining in the k-space domain or in the image domain (in SENSE), as well as methods which are hybrids. In SENSE imaging, coil sensitivity profiles are typically estimated from low-resolution reference data. This coil sensitivity information is then used to "unwrap" aliased pixels in image space using a direct inversion algorithm.

The present standard for the SENSE reference scan is a FFE (Fast Field Echo=gradient echo with small flip-angle excitation) acquisition protocol, which makes it very sensitive to susceptibility effects. When the susceptibility of metal parts compromises the quality of the SENSE reference scan, it may cause SENSE unfolding problems and signal voids resulting in an insufficient quality of the finally reconstructed MR images. Using a TSE (Turbo Spin Echo=spin echo with multiple 180° refocusing RF pulses) SENSE reference scan has been shown to be more robust against susceptibility effects, thereby reducing problems like incorrect SENSE unfolding and signal voids. However, a TSE SENSE reference scan may take a full minute or more, which is substantially longer than the standard FFE SENSE reference scan, which takes typically less than 10 seconds.

From the foregoing it is readily appreciated that there is a need for an improved parallel MR imaging technique that is sufficiently fast to enable multispectral imaging and that is robust against susceptibility effects.

In accordance with the invention, a method of MR imaging of at least a portion of a body placed in the examination volume of a MR device is disclosed. The method comprises the steps of:

subjecting the portion of the body to a first imaging sequence of RF pulses and switched magnetic field gradients, which imaging sequence is a stimulated echo sequence including:
   i) at least two preparation RF pulses radiated toward the portion of the body during a preparation period, and
   ii) one or more reading RF pulses radiated toward the portion of the body during an acquisition period temporally subsequent to the preparation period;
  acquiring one or more FID signals and one or more stimulated echo signals during the acquisition period by means of parallel signal acquisition via at least two RF coils having different spatial receive sensitivity profiles within the examination volume; and
  deriving the spatial receive sensitivity profiles of the at least two RF coils from the acquired FID signals and/or from the acquired stimulated echo signals.

In general, a stimulated echo sequence comprises three (for example 60° or) 90° RF pulses, wherein the first two RF pulses are preparation pulses. The first preparation RF pulse excites magnetic resonance and transforms the longitudinal nuclear magnetization into transverse nuclear magnetization. The second preparation RF pulse stores a fraction of the de-phased transverse nuclear magnetization along the longitudinal axis. In case of 90° RF pulses this fraction is almost half of the de-phased transverse magnetization. The third RF pulse is applied during the acquisition period which is temporally subsequent to the preparation period. The third RF pulse ("reading RF pulse") transforms the stored longitudinal nuclear magnetization into transverse nuclear magnetization again, thereby generating a so-called stimulated echo. Furthermore, it generates a free induction decay (FID) signal from the remaining longitudinal magnetisation. Other RF refocused echoes could potentially be generated by this three RF pulse sequence, but those are not of interest here and may be suppressed by appropriate gradient switching regimes running in parallel to the RF irradiation.

The stimulated echo MR signal together with the FID signal, which is also generated by the third RF pulse, is acquired according to the invention. MR imaging on the basis of the stimulated echoes can be accelerated by replacing the third RF pulse by a train of low-flip angle reading RF pulses, wherein each reading RF pulse refocuses only a small portion of the longitudinal nuclear magnetization stored after the preparation period.

The at least two preparation RF pulses used to store magnetization along the z-axis do not have to be of the same kind or flip angle. However, with respect to the mathematical treatment necessary to evaluate the measuring data, the choice of identical RF pulses and flip angles makes the formalism rather simple.

With appropriate parameters, the stimulated echo sequence of the invention is robust against susceptibility effects. According to the invention, the stimulated echo sequence with acquisition of the FID signals and the stimulated echo signals is used as a SENSE reference scan for MR imaging near metal. The sequence of the invention is robust against susceptibility effects and provides RF coil sensitivity information within seconds. This enables robust SENSE to accelerate multispectral MR imaging with the use of a fast SENSE reference scan.

In addition to RF receive coil sensitivity information, the sequence of the invention also provides information about $B_0$ distribution and transmit $B_1$ distribution.

An MR image can be reconstructed from the FID signals and another MR image can be reconstructed from the stimulated echo signals. After the MR image reconstruction, a transmit $B_1$ map can be derived from the voxel-wise intensity ratio of the two MR images reconstructed from the FID and stimulated echo signals, respectively. A plurality of FID signals and stimulated echo signals with appropriate phase encoding need to be acquired for generating a complete $B_1$ map (receive and/or transmit sensitivities).

According to another preferred embodiment of the invention, a $B_0$ map indicating the spatial distribution of the main magnetic field within the portion of the body is derived from the acquired FID and stimulated echo signals as well. It turns out that, by using appropriate parameters of the imaging sequence, not only a $B_1$ map, but also a $B_0$ map can be derived from the voxel-wise intensities of the FID and stimulated echo signals. It is an advantage of the invention that a $B_1$ map and a $B_0$ map can be acquired simultaneously without additional measurement steps. Therefore, as an additional value of the invention, without any additional scan time, the $B_0$ distribution information of the sequence can be used for automated determination of the required frequency coverage of subsequent diagnostic scans. The (multispectral) scan protocol can then (automatically) be adapted to meet this required frequency coverage in the minimal required scan duration. As the $B_0$ distribution is spatially dependent, it's even possible, if desired, to adapt the (multispectral) scan protocol to meet the required frequency coverage per slice.

In accordance with a preferred embodiment of the invention, the FID and the stimulated echo signals are acquired as gradient-recalled echo signals. The timing of the sequence can be adjusted such that susceptibility- and chemical shift-induced effects are essentially equal for both the FID and stimulated echo signals.

According to still another preferred embodiment of the invention, the proposed approach can be used for volumetric acquisitions. For volumetric applications, a multi-slice version of the proposed technique is advantageous. Therein, an appropriate slice order (e.g. measurement of the odd slices in a 3D stack in a first step and then the even ones in a subsequent measurement step), seems to be useful to avoid potential slice cross-talk. To ease the signal evaluation, as described below, the two preparation RF pulses of the stimulated echo sequence may excite a broader slice, (preferably with a slice thickness increased by a factor of two) than the reading RF pulses. This helps to avoid problems associated with imperfect slice profile excitation in signal evaluation for $B_1$ mapping.

According to a further preferred embodiment of the invention, the at least two preparation RF pulses each have a flip angle of 45°-90°. In this way, the amplitudes of the acquired stimulated echo signals are maximized which is advantageous in terms of signal-to-noise.

According to another preferred embodiment of the invention, a plurality of FID and stimulated echo MR signals are generated by means of a plurality of consecutive reading RF pulses, each having a flip angle of less than 90°, preferably less than 45°, most preferably less than 30°. As already mentioned above, a train of reading RF pulses having small flip angles can be used to achieve a fast readout of multiple FID and stimulated echo signals. Echo times as short as possible can be used to minimize $T_2^*$ relaxation.

According to yet another preferred embodiment of the invention, switched magnetic field gradients are applied during the preparation period after the two preparation RF pulses in order to spoil residual nuclear magnetization.

According to still another preferred embodiment of the invention, the FID signals and/or the stimulated echo signals are acquired via the at least two RF coils having different spatial receive sensitivity profiles and, in parallel or sequentially, via at least one volume RF coil having a substantially homogeneous spatial sensitivity profile within the examination volume, wherein the spatial receive sensitivity profiles of the RF coils are derived by comparing the signals acquired via RF coils having different spatial sensitivity profiles with the signals acquired via the volume RF coil. For example, the signal acquisition according to the invention may be repeated, at least two times, in the first acquisition using the volume RF coil for reception in the second using the RF coils having different spatial sensitivities. In an alternative approach, the RF coils to be used for MR signal acquisition can be switched during a stimulated echo readout according to the invention. In this way, motion artefacts can be reduced, when the data interleaving process also checks for signal inconsistencies. Moreover, the receive RF coil sensitivity mapping can be performed according to the invention in a single acquisition step, using the volume RF coil and the RF coils having different receive sensitivity profiles (e.g. array RF coils) simultaneously, provided a sufficient RF coil decoupling can be achieved.

According to a further preferred embodiment of the invention, the parameters of the first imaging sequence are selected such that the temporal spacing between the two preparation RF pulses equals the echo time of the stimulated echo. This timing scheme preserves the spin echo properties of the stimulated echo. Hence, spatial phase variations due to static inhomogeneities of the main magnetic field are fully compensated by refocusing of the spin phases, allowing to derive metal-resistant spatial sensitivity profiles of the RF coils from the stimulated echo signals. The determination of a $B_1$ map and a $B_0$ map remains possible, except for the vicinity of the metal parts, where the strong susceptibility effects may degrade the FID signal. In case of strong susceptibility effects, the signal analysis for deriving the spatial sensitivity profiles should be based only on the stimulated echo signals. If metal implants or other sources of strong main magnetic field changes are not present, additionally also the FID signals can be used to estimate the RF receive coil sensitivity profiles in order to improve the signal-to-noise ratio.

In a preferred embodiment, the method of the invention further comprises the steps of:

subjecting the portion of the body to a second imaging sequence of RF pulses and switched magnetic field gradients;

acquiring a MR signal data set by means of parallel signal acquisition via the at least two RF coils with sub-sampling of k-space; and reconstruction of a MR image from the MR signal data set and from the spatial sensitivity profiles of the at least two RF coils.

In this embodiment of the invention, the final (diagnostic) MR image is reconstructed, for example by using the SENSE algorithm, from the MR signal data set acquired by parallel (i.e. accelerated) imaging using sub-sampling and from the spatial sensitivity profiles derived from the simulated echo acquisition. In order to enable fast imaging, the image resolution of the first imaging sequence (reference scan) can be chosen to be lower than the image resolution of the second imaging sequence (diagnostic scan). The reference scan may be performed prior to or after the diagnostic scan.

In accordance with another preferred embodiment of the invention, the second imaging sequence is a multispectral imaging sequence. The above referenced multispectral imaging techniques like SEMAC and MAVRIC can be used in order to enable MR imaging near metal parts. The scan duration can be kept within reasonable limits by using SENSE in combination with the stimulated echo reference scan, which is fast and robust against susceptibility effects according to the invention.

The method of the invention described thus far can be carried out by means of a MR device including at least one main magnet coil for generating a uniform steady magnetic field within an examination volume, a number of gradient coils for generating switched magnetic field gradients in different spatial directions within the examination volume, at least one RF coil for generating RF pulses within the examination volume and/or for receiving MR signals from a body of a patient positioned in the examination volume, a control unit for controlling the temporal succession of RF pulses and switched magnetic field gradients, and a reconstruction unit for reconstructing MR images from the received MR signals. The method of the invention is preferably implemented by a corresponding programming of the reconstruction unit and/or the control unit of the MR device.

The methods of the invention can be advantageously carried out in most MR devices in clinical use at present. To this end it is merely necessary to utilize a computer program by which the MR device is controlled such that it performs the above-explained method steps of the invention. The computer program may be present either on a data carrier or be present in a data network so as to be downloaded for installation in the control unit of the MR device.

BRIEF DESCRIPTION OF THE DRAWINGS

The enclosed drawings disclose preferred embodiments of the present invention. It should be understood, however, that the drawings are designed for the purpose of illustration only and not as a definition of the limits of the invention. In the drawings.

DETAILED DESCRIPTION OF EMBODIMENTS

Figure 1:
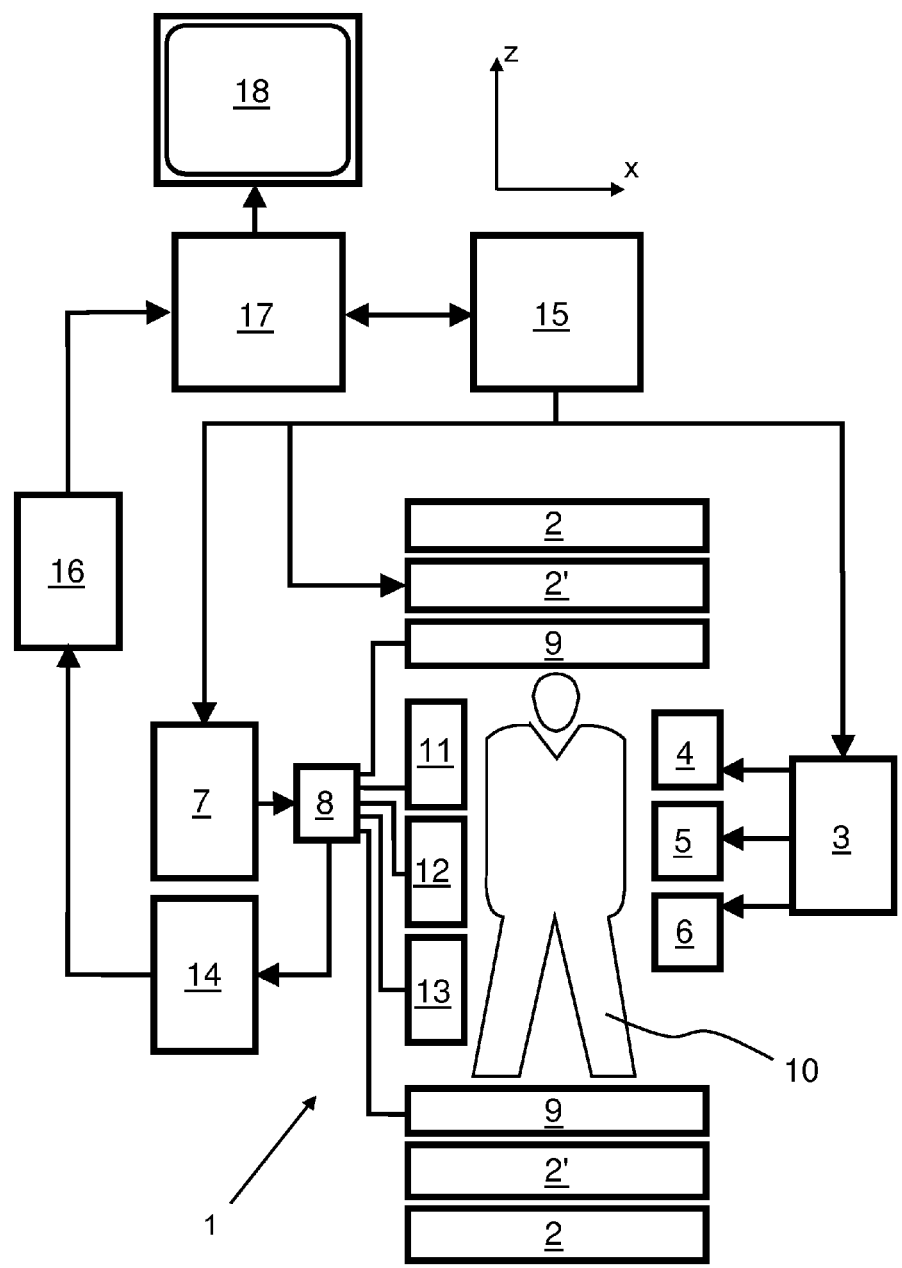
FIG. 1 schematically shows a MR device for carrying out the methods of the invention.

With reference to FIG. 1, a MR device 1 is shown. The device comprises superconducting or resistive main magnet coils 2 such that a substantially uniform, temporally constant main magnetic field $B_0$ is created along a z-axis through an examination volume. The device further comprises a set of ($1^{st}$, $2^{nd}$, and—where applicable—$3^{rd}$ order) shimming coils 2', wherein the current flow through the individual shimming coils of the set 2' is controllable for the purpose of minimizing $B_0$ deviations within the examination volume.

A magnetic resonance generation and manipulation system applies a series of RF pulses and switched magnetic field gradients to invert or excite nuclear magnetic spins, induce magnetic resonance, refocus magnetic resonance, manipulate magnetic resonance, spatially and otherwise encode the magnetic resonance, saturate spins, and the like to perform MR imaging.

More specifically, a gradient pulse amplifier 3 applies current pulses to selected ones of whole-body gradient coils 4, 5 and 6 along x, y and z-axes of the examination volume. A digital RF frequency transmitter 7 transmits RF pulses or pulse packets, via a send-/receive switch 8, to a body RF coil 9 to transmit RF pulses into the examination volume. A typical MR imaging sequence is composed of a packet of RF pulse segments of short duration which taken together with each other and any applied magnetic field gradients achieve a selected manipulation of nuclear magnetic resonance. The RF pulses are used to saturate, excite resonance, invert magnetization, refocus resonance, or manipulate resonance and select a portion of a body 10 positioned in the examination volume.

For generation of MR images of regions of the body 10 by means of parallel imaging, a set of local array RF coils 11, 12, 13 are placed contiguous to the region selected for imaging. The array RF coils 11, 12, 13 can be used to receive MR signals induced by body-coil RF transmissions.

The resultant MR signals are picked up by the body RF coil 9 and/or by the array RF coils 11, 12, 13 and demodulated by a receiver 14 preferably including a preamplifier (not shown). The receiver 14 is connected to the RF coils 9, 11, 12 and 13 via send-/receive switch 8.

A host computer 15 controls the current flow through the shimming coils 2' as well as the gradient pulse amplifier 3 and the transmitter 7 to generate any of a plurality of MR imaging sequences, such as echo planar imaging (EPI), echo volume imaging, gradient and spin echo imaging, fast spin echo imaging, and the like. For the selected sequence, the receiver 14 receives a single or a plurality of MR data lines in rapid succession following each RF excitation pulse. A data acquisition system 16 performs analog-to-digital conversion of the received signals and converts each MR data line to a digital format suitable for further processing. In modern MR devices the data acquisition system 16 is a separate computer which is specialized in acquisition of raw image data.

Ultimately, the digital raw image data is reconstructed into an image representation by a reconstruction processor 17 which applies appropriate reconstruction algorithms, such like SENSE. The MR image may represent a planar slice through the patient, an array of parallel planar slices, a three-dimensional volume, or the like. The image is then stored in an image memory where it may be accessed for converting slices, projections, or other portions of the image representation into appropriate format for visualization, for example via a video monitor 18 which provides a man-readable display of the resultant MR image.

Figure 2:
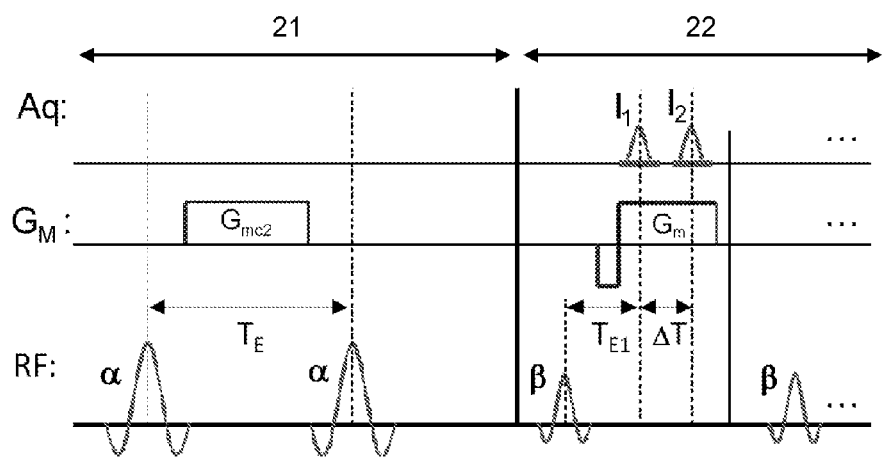
FIG. 2 shows a diagram illustrating a first imaging sequence according to the invention.

FIG. 2 shows a schematic diagram illustrating a first imaging sequence according to the invention which is applied as a SENSE reference scan. The depicted imaging sequence is a stimulated echo sequence which is subdivided into a preparation period 21 and an acquisition period 22. Two preparation RF pulses having a flip angle of α are applied during the preparation period 21. The two preparation RF pulses are separated by a time interval $T_E$. A de-phaser magnetic field gradient $G_{mc2}$ is applied between the two preparation RF pulses. A sequence of reading RF pulses having flip-angle β are generated during the acquisition period 22, which is temporally subsequent to the preparation period 21. An FID signal $I_1$ and a stimulated echo signal $I_2$ are acquired after each reading pulse as gradient-recalled echoes.

Directly after the preparation sequence 21, the longitudinal magnetization is given by:

$$M_{z1} = \cos^2(\alpha) \cdot M_0$$
$$M_{z2} = \frac{1}{2}\sin^2(\alpha) \cdot M_0,$$

wherein $M_{z1}$ and $M_{z2}$ denote the un-prepared (i.e. in-phase) and the stimulated echo-prepared (i.e. de-phased) longitudinal magnetization, respectively. In accordance with the invention, both the FID signal $I_1$ generated from $M_{z1}$ and the stimulated echo signal $I_2$ generated from Mz2 are acquired at different points in time TE1 and TE1+T, respectively. The delay T between the two echoes I1, I2 is determined by the relation:

$$\Delta T = A_{mc2}/G_m,$$

wherein Amc2 denotes the gradient-time area of the de-phaser gradient Gmc2 and Gm denotes the strength of the readout magnetic field gradient.

According to the invention, the timing scheme TE=TE1+ΔT can be employed, which fully preserves the spin echo properties of the stimulated echo. Hence, static inhomogeneities of the main magnetic field $B_0$ are fully refocused, allowing metal-resistant SENSE reference scan data to be derived from the stimulated echo signal $I_2$.

If the MR signal acquisition by means of the first imaging sequence is repeated, at least two times, in the first acquisition using the body RF coil 9 for reception in the second using the array RF coils 11, 12, 13, the receive RF coil sensitivity profiles can be derived. In case of strong susceptibility effects, the corresponding signal analysis should be based only on the stimulated echo signal $I_2$.

The (unknown) flip angle α of the stimulated echo preparation RF pulses (and thus the transmit $B_1$ map of the used transmit coil) can be derived from the ratio of the acquired echo signals according to:

$$\alpha = \arctan\sqrt{2|I_2/I_1|}$$

The mirrored phase of the stimulated echo signal $I_2$ may be further employed to derive a $B_0$ phase map:

$$\varphi_{B_0} = \arg(I_1 \cdot I_2^*)$$

After application of the first imaging sequence as a SENSE reference scan, a second imaging sequence (not depicted) is performed as a diagnostic scan with sub-sampling of k-space. The corresponding diagnostic MR image is then reconstructed, by using the SENSE algorithm, from the MR signal data set acquired during the diagnostic scan and from the spatial sensitivity profiles derived from the stimulated echo acquisition of the reference scan. The second imaging sequence can be a multispectral imaging sequence in order to improve MR image quality near metal parts. Though multispectral imaging sequences are typically associated with long scan durations, the scan duration is kept within reasonable limits by using SENSE parallel imaging in combination with the stimulated echo reference scan, which is fast and robust against susceptibility effects.

The afore-described technique of the invention improves the applicability of MR imaging near metal, which may be part of but not limited to: cobalt-chrome, titanium, stainless steel, zirconium oxide. Application areas include, for example, diagnosis in the following cases:

Evaluation of post-operative complications, including infections, integrity of surrounding soft tissue in the presence of metal objects that may include orthopedic implants for e.g. knee, hip, rib, ankle, or oncology bone reconstruction, fixing plates, screws, stents or MR safe implanted electrodes, etc.

Application of super-paramagnetic agents (e.g. iron disposition). Diagnostic imaging in the presence of bullets or shrapnel, e.g. resulting from surgery, trauma, profession in metal processing industry etc.

Therapy applications of the method of the invention include imaging in the proximity of interventional instruments, for example seeds implanted for brachytherapy, needle tracking for biopsy or deep brain stimulation, and other areas in which susceptibility artefacts limit the quality and thus the value of MR images.

The invention claimed is:

1. A method of magnetic resonance (MR) imaging of at least a portion of a body placed within an examination volume of a MR device, the MR imaging being robust against susceptibility effects, the method comprising:
   subjecting the portion of the body to a first imaging sequence of radio frequency (RF) pulses and switched magnetic field gradients, the first imaging sequence is being a stimulated echo sequence including:
   i) radiating two preparation radio frequency (RF) pulses ($\alpha$) provided by a RF transmitter toward the portion of the body, and applying a de-phaser magnetic field gradient provided by a gradient pulse amplifier to the portion of the body between the two preparation RF pulses, during a preparation period; and
   ii) radiating at least one RF pulse ($\beta$) provided by the RF transmitter toward the portion of the body, and obtaining a readout magnetic field gradient, during an acquisition period temporally subsequent to the preparation period;
   acquiring a free induction delay (FID) signal ($I_1$) and a stimulated echo signal ($I_2$) as gradient-recalled echoes following each of the at least one RF pulse ($\beta$) during the acquisition period, using parallel signal acquisition via at least two RF coils having different spatial sensitivity profiles within the examination volume, wherein a time delay between the acquired (FID) signal ($I_1$) and the acquired stimulated echo signal ($I_2$) is based on a gradient-time area of the de-phaser magnetic field gradient and the readout magnetic field gradient; and
   deriving the spatial sensitivity profiles of the at least two RF coils from at least one of the acquired FID signal ($I_1$) and the acquired stimulated echo signal ($I_2$)
   reconstructing a MR image from a MR signal data set acquired from the derived spatial sensitivity profiles.

2. The method of claim 1, further comprising deriving a $B_1$ map, indicating a spatial distribution of a RF field of the RF pulses, from the acquired at least one FID signal ($I_1$) and at least one stimulated echo ($I_2$) signal.

3. The method of claim 1, wherein the at least two preparation RF pulses ($\alpha$) each have a flip angle in a range of 450-900.

4. The method of claim 1, wherein a plurality of FID signals ($I_1$) and a plurality of stimulated echo signals ($I_2$) are generated by a corresponding plurality of consecutive reading RF pulses ($\beta$), each having a flip angle of less than 90°.

5. The method of claim 1, further comprising deriving a $B_0$ map, indicating the spatial distribution of the main magnetic field, from the acquired FID signal ($I_1$) and the acquired stimulated echo ($I_2$) signal.

6. The method of claim 1, wherein the FID signal ($I_1$) and the stimulated echo signal ($I_2$) are acquired via the at least two RF coils having different spatial sensitivity profiles and via at least one volume RF coil having a substantially homogeneous spatial sensitivity profile within the examination volume, and wherein the spatial sensitivity profiles of the RF coils are derived by comparing the FID and stimulated echo signals ($I_1$, $I_2$) acquired via the RF coils having different spatial sensitivity profiles with the FID and stimulated echo signals ($I_1$, $I_2$) acquired via the volume RF coil.

7. The method of claim 6, wherein the parameters of the first imaging sequence are selected such that the temporal spacing between the two preparation RF pulses ($\alpha$) equals the echo time of the stimulated echo.

8. The method of claim 7, further comprising:
   subjecting the portion of the body to a second imaging sequence of RF pulses and switched magnetic field gradients;
   acquiring a MR signal data set by parallel signal acquisition via the at least two RF coils with sub-sampling of k-space; and
   reconstructing a MR image from the MR signal data set and from the spatial sensitivity profiles of the at least two RF coils.

9. The method of claim 8, wherein the MR image is reconstructed by using at least one of a SENSE algorithm, SMASH algorithm and a GRAPPA algorithm.

10. The method of claim 8, wherein the second imaging sequence is a multispectral imaging sequence.

11. A magnetic resonance (MR) device comprising:
   at least one main magnet coil for generating a uniform, steady magnetic field within an examination volume;
   a plurality of gradient coils for generating switched magnetic field gradients in different spatial directions within the examination volume;
   a body radio frequency (RF) coil for generating RF pulses within the examination volume;
   at least two RF coils having different spatial sensitivity profiles within the examination volume for receiving MR signals from at least a portion of a body positioned in the examination volume;
   a host computer for controlling a temporal succession of RF pulses and switched magnetic field gradients, and for deriving the spatial sensitivity profiles of the at least two RF coils; and
   a reconstruction unit for reconstructing MR images from the received MR signals provided by the at least two RF coils using the derived spatial sensitivity profiles,
   wherein the host computer executes a computer program for performing the following steps:
   subjecting the portion of the body to a first imaging sequence of RF pulses and switched magnetic field gradients, the first imaging sequence being a stimulated echo sequence including:
   i) radiating two preparation RF pulses ($\alpha$) from the body RF coil toward the portion of the body, and applying a de-phaser magnetic field gradient between the two preparation RF pulses during a preparation period, and
   ii) radiating one or more reading RF pulses ($\beta$) from the body RF coil toward the portion of the body and followed by a readout magnetic field gradient during an acquisition period temporally subsequent to the preparation period;
   acquiring a free induction delay (FID) signal ($I_1$) and a stimulated echo signal ($I_2$) during the acquisition period using parallel signal acquisition via the at least two RF coils, wherein a time delay between the acquired FID signal ($I_1$) and the acquired stimulated echo signal ($I_2$)

is based on a gradient-time area of the de-phaser magnetic field gradient and the readout magnetic field gradient; and deriving the spatial sensitivity profiles of the at least two RF coils from at least one of the acquired FID signal ($I_1$) and the acquired stimulated echo signal ($I_2$).

12. A computer readable medium, executable by a computer processor of a magnetic resonance (MR) device, for providing MR imaging robust against susceptibility effects, the computer readable medium comprising:

code for causing generation of a first imaging sequence of radio frequency (RF) pulses and switched magnetic field gradients, the first imaging sequence being a stimulated echo sequence including:

i) radiating two preparation RF pulses (α) and applying a de-phaser magnetic field gradient between the two preparation RF pulses during a preparation period, and ii) radiating a reading RF pulse (β), followed by a readout magnetic field gradient during an acquisition period temporally subsequent to the preparation period;

code for causing acquisition of a free induction delay (FID) signal ($I_1$) and a stimulated echo signal ($I_2$) during the acquisition period using parallel signal acquisition via at least two RF coils, wherein a time delay between the acquired FID signal ($I_1$) and the acquired stimulated echo signal ($I_2$) is based on a gradient-time area of the de-phaser magnetic field gradient and the readout magnetic field gradient;

code for deriving the spatial sensitivity profiles of the at least two RF coils from at least one of the acquired FID signal ($I_1$) and the acquired stimulated echo signal ($I_2$); and code for reconstructing a MR image from a MR signal data set acquired using the derived spatial sensitivity profiles.

13. The method of claim 1, wherein a plurality of FID signals ($I_1$) and a plurality of stimulated echo signals ($I_2$) are generated by a corresponding plurality of consecutive reading RF pulses (β), each having a flip angle of less than 45°.

14. The method of claim 1, wherein a plurality of FID signals ($I_1$) and a plurality of stimulated echo signals ($I_2$) are generated by a corresponding plurality of consecutive reading RF pulses (β), each having a flip angle of less than 30°.

15. The method of claim 1, wherein:

when a source of strong main magnetic field changes is present in the body, causing strong susceptibility effects, the spatial sensitivity profiles of the at least two RF coils are derived based only on the acquired stimulated echo signal ($I_2$), and when the source of strong main magnetic field changes is not present in the body, the spatial sensitivity profiles of the at least two RF coils are derived based, at least in part, on the acquired FID signal ($I_1$).

16. The method of claim 15, wherein the source of strong main magnetic field changes in the body comprises a metal implant.

* * * * *